_(12)_ United States Patent
Schuele (10) Patent No.: US 10,835,226 B2
(45) Date of Patent: Nov. 17, 2020

(54) FLEXIBLE ARM AND METHOD OF USING

(71) Applicant: pro med instruments GmbH, Freiburg im Breisgau (DE)

(72) Inventor: Matthias E. Schuele, Freiburg (DE)

(73) Assignee: pro med instruments GmbH, Freiburg im Breisgau (DE)

( * ) Notice: Subject to any disclaimer, the term of this patent is extended or adjusted under 35 U.S.C. 154(b) by 596 days.

(21) Appl. No.: 14/210,988

(22) Filed: Mar. 14, 2014

(65) Prior Publication Data

US 2014/0275799 A1 Sep. 18, 2014

Related U.S. Application Data

(60) Provisional application No. 61/798,369, filed on Mar. 15, 2013.

(51) Int. Cl.
*A61B 17/56* (2006.01)
*A61B 1/32* (2006.01)
(Continued)

(52) U.S. Cl.
CPC .............. *A61B 17/02* (2013.01); *A61B 90/50* (2016.02); *F16M 11/14* (2013.01); *F16M 11/40* (2013.01);
(Continued)

(58) Field of Classification Search
CPC .......... A61B 17/02; A61B 2017/00314; A61B 2017/0243; A61B 2090/508; A61B 90/50;
(Continued)

(56) References Cited

U.S. PATENT DOCUMENTS 599,543 A * 2/1898 Whitaker ............... F16M 11/40
248/160
3,096,962 A 7/1963 Meijs
(Continued)

FOREIGN PATENT DOCUMENTS

JP S53-109081 A 9/1978
JP 2003-529403 A 10/2003
(Continued)

OTHER PUBLICATIONS

International Search Report and Written Opinion dated Nov. 10, 2014 for Application No. PCT/IB2014/001172.
(Continued)

*Primary Examiner* — Jessica Weiss
(74) *Attorney, Agent, or Firm* — Frost Brwon Todd LLC (57) ABSTRACT

A flexible arm for use in a medical procedure includes a plurality of bushings and a plurality of double-ball members engaged with one another to thereby provide flexibility to the flexible arm. The double-ball members include a concave bore having a convex interior surface. The flexible arm further includes a wire extending through the concave bore of the double-ball members. An exterior diameter of the wire closely approximates or matches an interior diameter of the concave bore at its smallest point such that the curved members are operable to guide the wire as the flexible arm is flexed. The wire may be adjusted to thereby manipulate the amount of engagement between the bushings and the double-ball members to thereby manipulate the flexibility of the flexible arm.

20 Claims, 5 Drawing Sheets

(51) Int. Cl.
*A61B 17/02* (2006.01)
*A61B 17/00* (2006.01)
*F16M 11/14* (2006.01)
*F16M 11/40* (2006.01)
*A61B 90/50* (2016.01)

(52) U.S. Cl.
CPC ............ *A61B 2017/00314* (2013.01); *A61B 2017/0243* (2013.01); *A61B 2090/508* (2016.02); *F16M 2200/02* (2013.01)

(58) Field of Classification Search
CPC .... A61B 17/0206; F16M 11/04; F16M 11/06; F16M 11/08; F16M 11/10; F16M 11/12; F16M 11/14; F16M 11/40; F16M 11/041; F16M 11/043; F16M 11/121
USPC ............ 600/201, 209, 37, 228–230; 901/17; 269/45, 58, 71
See application file for complete search history.

(56) References Cited

U.S. PATENT DOCUMENTS

| | | | |
|---|---|---|---|
| 3,584,822 A * | 6/1971 | Oram .................... | F16M 11/40 248/160 |
| 4,010,745 A | 3/1977 | Height | |
| 4,949,927 A * | 8/1990 | Madocks ............... | F16M 11/40 248/160 |
| 5,348,259 A | 9/1994 | Blanco et al. | |
| 5,865,730 A * | 2/1999 | Fox .................... | A61B 17/0218 600/201 |
| 5,947,896 A * | 9/1999 | Sherts ................ | A61B 17/0293 600/229 |
| 6,338,738 B1 | 1/2002 | Bellotti et al. | |
| 6,345,793 B1 | 2/2002 | Mauro | |
| 6,849,044 B1 * | 2/2005 | Voss ...................... | A61B 17/02 403/90 |
| 7,250,028 B2 * | 7/2007 | Julian ................. | A61B 17/00234 600/228 |
| 8,230,863 B2 * | 7/2012 | Ravikumar ........... | A61B 90/57 128/845 |
| 8,277,476 B2 * | 10/2012 | Taylor .............. | A61B 17/00234 606/191 |
| 8,808,176 B2 * | 8/2014 | Menendez ........... | A61B 17/175 600/227 |
| 8,840,077 B2 * | 9/2014 | Von Pechmann ...... | F16M 11/40 248/288.31 |
| 9,221,179 B2 * | 12/2015 | Hinman .................. | A61B 17/29 403/56 |
| 9,237,933 B2 * | 1/2016 | Agbodoe ............... | F16M 11/40 248/160 |
| 2002/0058856 A1 * | 5/2002 | Peng ..................... | A61B 17/02 600/37 |
| 2002/0115911 A1 * | 8/2002 | Knight .................. | A61B 17/02 600/228 |
| 2003/0083555 A1 * | 5/2003 | Hunt ..................... | A61B 17/02 600/229 |
| 2003/0165352 A1 * | 9/2003 | Ibrahim ................ | A61B 17/02 403/56 |
| 2003/0180088 A1 * | 9/2003 | Carnevali ............... | F16M 11/14 403/56 |
| 2003/0216619 A1 * | 11/2003 | Scirica ............... | A61B 17/0293 600/229 |
| 2006/0016006 A1 * | 1/2006 | Whitmore, III ...... | A61B 6/0442 5/601 |
| 2007/0055291 A1 * | 3/2007 | Birkmeyer ............. | A61B 90/13 606/130 |
| 2008/0132897 A1 * | 6/2008 | Livorsi ................ | A61B 17/154 606/88 |
| 2013/0099081 A1 * | 4/2013 | Agbodoe ............... | F16M 11/40 248/276.1 |

FOREIGN PATENT DOCUMENTS

WO   WO 93/15668         8/1993
WO   WO 01/17437 A2     3/2001

OTHER PUBLICATIONS

Japanese Office Action, Notice of Rejection, dated Dec. 12, 2017 for Application No. JP 2015-562401, 7 pgs.
Japanese Office Action, Notice of Allowance, dated Nov. 13, 2018 for Application No. JP 2015-562401, 4 pgs.

* cited by examiner

FLEXIBLE ARM AND METHOD OF USING

PRIORITY

This application claims priority to U.S. Provisional Pat. Application No. 61/798,369, entitled "Flexible Arm and Method of Using," filed Mar. 15, 2013, the disclosure of which is incorporated by reference herein.

BACKGROUND

In certain surgical procedures, accessories such as retractor blades or spatulas are used to assist the surgeon or other medical personnel to pull or retract tissue or parts of the body. In some instances, these blades can be used with flexible arms or retractor arms to provide a range of adjustability when positioning the blades. These flexible arms are mountable to other structures (e.g. an OR table, a head fixation device such as a skull clamp, or a retractor system such as a halo retractor system) to secure one end of them during the procedure. The arms themselves include actuators that allow the arm to be adjusted from one position to another position and then locked in the desired position.

While a variety of flexible arms or retractor arms may have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
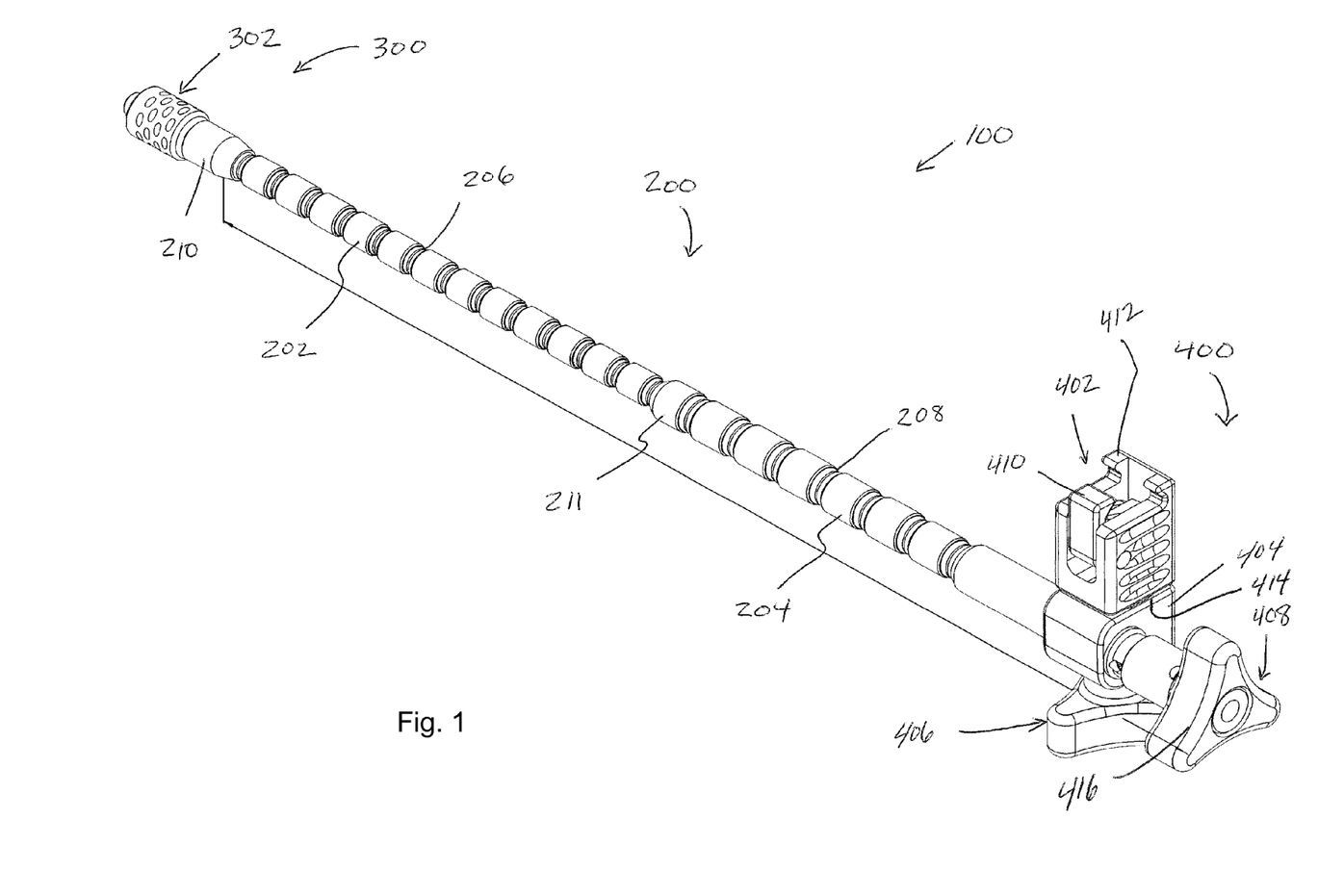
FIG. 1 depicts a perspective view of an example of a flexible arm.

FIG. 1 illustrates an example flexible arm (100). Flexible arm (100) comprises central portion (200), distal portion (300), and proximal portion (400). Central portion (200) comprises several first bushings (202) and several second bushings (204) that are larger than first bushings (202) as shown. Central portion (200) also comprises several first curved members (206) and several second curved members (208) that are larger than first curved members (206). In some versions, first and second curved members (206, 208) may be referred to as double-ball structures or bone-shaped structures. Near the end of central portion (200) toward distal portion (300) is linking member (210). Linking member (210) connects distal portion (300) to the remaining portions of flexible arm (100). Near the middle of central portion (200) is reducer (211) where flexible arm (100) transitions from second bushings (204) and second curved members (208) to first bushings (202) and first curved members (206).

Distal portion (300) comprises adapter (302) that is configured to connect with an accessory, e.g. a surgical retractor blade or spatula. Adapter (302) comprises outer member (304) and receiving member (306). Receiving member (306) is configured to accept and selectively retain an accessory, e.g. a surgical retractor blade or spatula.

Proximal portion (400) comprises attachment member (402), body portion (404), first actuator (406), and second actuator (408). Attachment member (402) includes movable jaw (410) that is configured to clamp onto a mounting structure (not shown) with the assistance of fixed jaw (412). A starburst interface (414) is present between attachment member (402) and body portion (404) such that attachment member (402) is rotatably adjustable relative to body portion (404). First actuator (406) is operable to selectively engage starburst interface (414) for rotational adjustment and fixation of attachment member (402). First actuator (406) is further operable to control movement of jaw (410) to allow attachment member (402) to selectively attach with a mounting structure.

Figure 2:
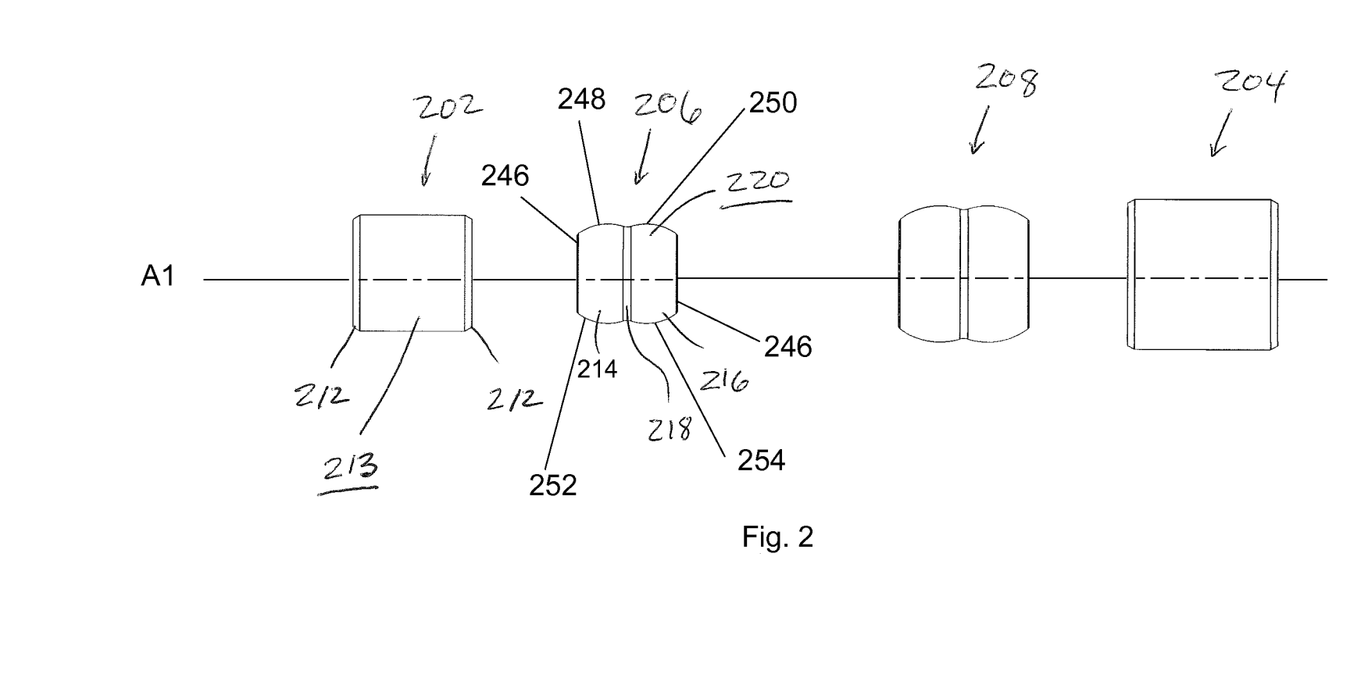
FIG. 2 depicts a side view of separated bushings and curved members that comprise the length of a central portion of the flexible arm of FIG. 1.

FIG. 2 illustrates example first and second bushings (202, 204) and first and second curved members (206, 208) of central portion (200) of flexible arm (100). In the illustrated view, first and second bushings (202, 204) and first and second curved members (206, 208) are shown spaced apart from one another to provide a more clear illustration of their shapes. Because the shapes are the same or substantially the same between the two sizes of these components, further description will focus on first bushing (202) and first curved member (206), it being understood that the description applies equally to second bushing (204) and second curved member (208).

First bushing (202) comprises a cylinder shape with tapered edges (212) and outer surface (213). First curved member (206) comprises a multi-curve somewhat cylindrical shape with a first curved portion (214), a second curved portion (216), and a center portion (218) located between first and second curved portions (214, 216). In some versions center portion (218) is configured as a cylinder having a relatively short length compared to the length of first and second curved portions (214, 216). In some other versions center portion (218) is merely the area or point of intersection where first and second curved portions (214, 216) meet. Referring again to FIG. 2, first curved member (206) has a varying outer diameter that, from one end to the other end, increases then decreases, then increases again then decreases again. In some versions, along all or a part of center portion (218) the outer diameter of first curved member (206) may remain constant. These features of first curved member (206) give first curved member (206) an appearance or shape of portions of two spherical members that have been joined together, hence the reference above to the double-ball shape or bone shape. Stated another way, first curved member (206) comprises a shape having two overlapping spherical members. First curved member (206) further comprises outer surface (220).

First curved member (206) can further be described as having ends (246) that are perpendicular to longitudinal axis (A1). First curved member (206) has a profile seen from its side view in FIG. 2. In the illustrated example, the profile of first curved member (206) is defined by more than one arc. For instance, first arc (248), second arc (250), third arc (252), and fourth arc (254) substantially define the profile of first curved member (206) when viewed from the side as shown in FIG. 2. Also, along a top of the profile, first arc (248) joins or connects with second arc (250), and similarly third arc (252) joins or connects with fourth arc (254) along a bottom of the profile. In some versions, first arc (248) and second arc (250) are indirectly joined as both can connect to a linear segment near central portion (218). In such versions, similarly third arc (252) and fourth arc (254) are indirectly joined as both can connect to a linear segment near central portion (218).

When considering first curved member (206), in its three dimensional form, first arc (246) and third arc (250) of the profile view represent the curved or arcuate outer surface of first curved portion (214). Similarly, second arc (248) and fourth arc (252) of the profile view represent the curved or arcuate outer surface of second curved portion (216). Thus outer surface (220) of first curved member (206) is comprised of a curved outer surface of first curved portion (214) and a curved outer surface of second curved portion (216). In some versions, outer surface (220) is additionally comprised of an outer surface of center portion (218).

Figure 3:
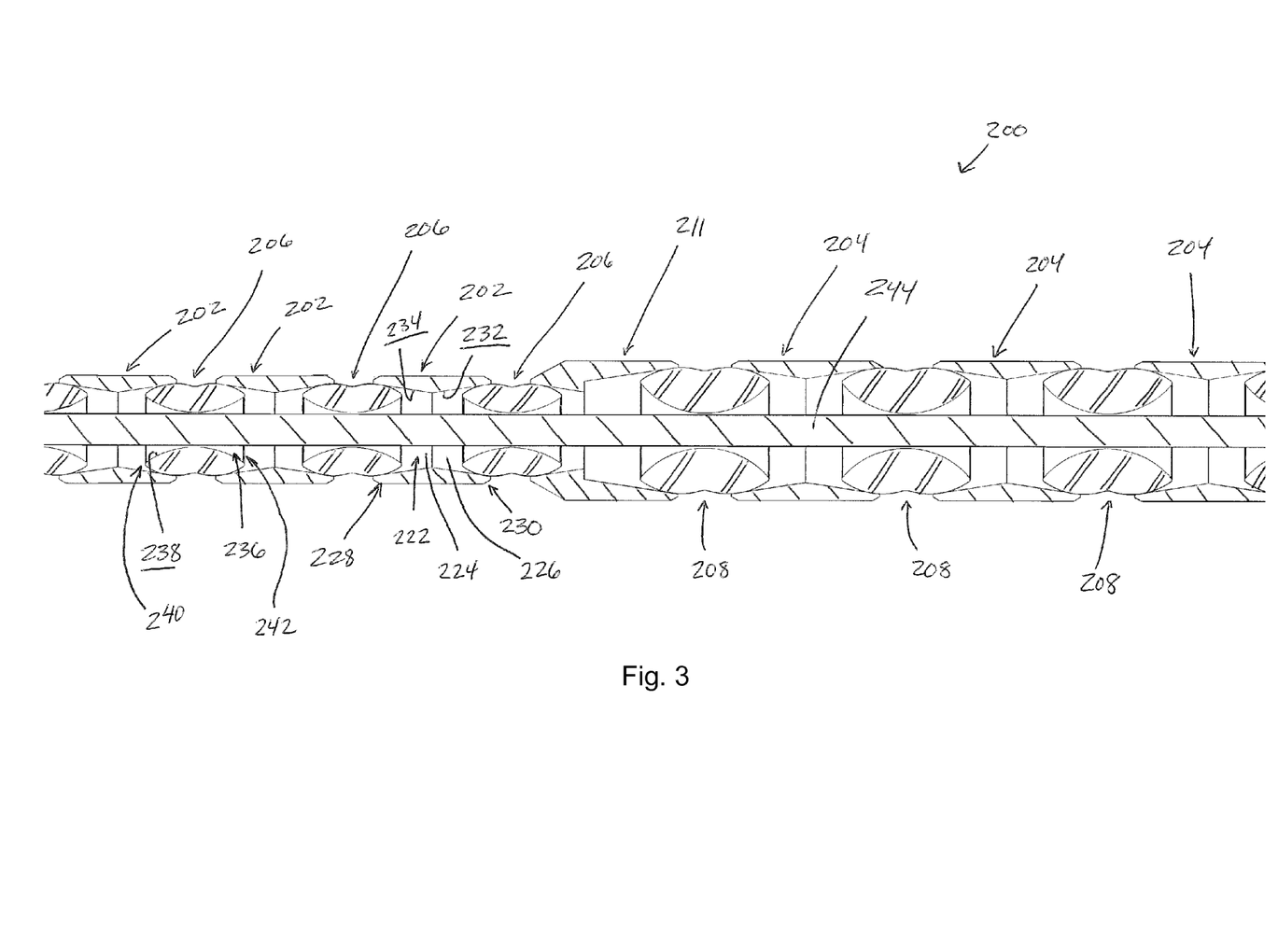
FIG. 3 depicts a side section view of a central portion of the flexible arm of FIG. 1.

FIG. 3 illustrates an example cross section view of a part of central portion (200) of flexible arm (100). As shown, first bushing (202) comprise bore (222) that extends through first bushing (202). Bore (222) comprises first region (224) and second region (226). As illustrated, first region (224) and second region (226) are mirror images and hence the description of one applies to the description of the other. First region (224) has a greater diameter at distal end (228) of first bushing (202), and the diameter then decreases to a minimum near the center of first bushing (202) where first region (224) of bore (222) meets second region (226) of bore (222). When moving proximally through the second region (226) of bore (222) the diameter increases until reaching proximal end (230) of first bushing (202).

Figure 4:
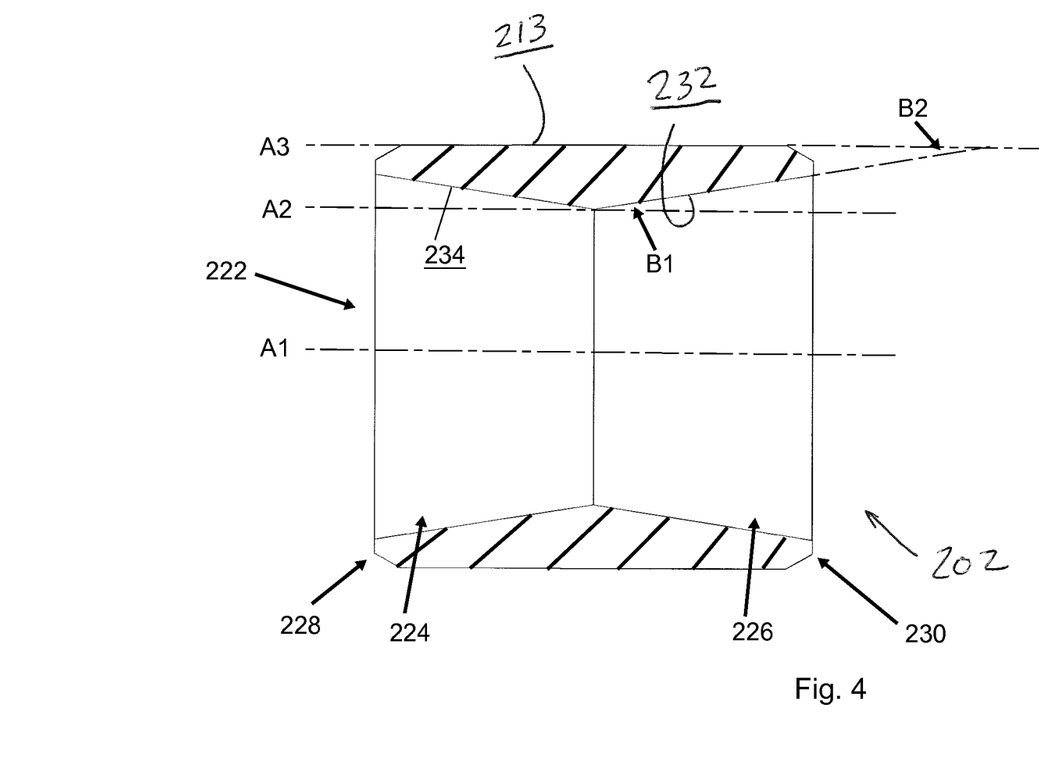
FIG. 4 depicts a side section view of a bushing showing an angle of the interior surface of the bushing.

Interior surfaces (232, 234) of first bushing (202) define bore (222). Furthermore interior surfaces (232, 234) are angled and curved surfaces, in other words conical surfaces, that are configured to receive first curved member (206). In section across the longitudinal center of bushing (202) (as depicted in FIG. 4), interior surfaces (232, 234) are shown with a linear profile. Interior surface (232) creates or defines an angle (B1) with longitudinal axis (A2). Similarly, interior surface (234) does the same thing on the other opposite end of first bushing (202). In the present example, longitudinal axis (A2) is parallel with longitudinal axis (A1), and furthermore longitudinal axes (A1) and (A2) are substantially parallel with outer surface (213) of first bushing (202). The line representing interior surface (232) in the section view of FIG. 4 shows that interior surface (232) creates or defines an angle (B2) at the intersection with a longitudinal axis (A3) that extends from outer surface (213). Similarly, interior surface (234) does the same thing on the other opposite end of first bushing (202). In the illustrated version, where longitudinal axes (A2) and (A3) are parallel, angles (B1) and (B2) are alternate interior angles that are the same.

In some versions, the angle created from interior surfaces (232, 234) respectively with outer surface (213) of first bushing (202) (i.e. angle (B2) as shown in the side cross section of FIG. 4), is between and including 0 and 20 degrees. In other versions this angle is less than 20 degrees. In some other versions, this angle is between and including 9 and 15 degrees. Still in some other versions, this angle is between and including 8 and 12 degrees. Of course in other versions any angle within or outside the above stated ranges can be used so long as the angle is not too small where the coefficient of friction of the materials used causes the frictional forces due to the contact of interior surfaces (232, 234) with outer surface (220) to be too great such that it becomes overly difficult to adjust flex arm (100). In instances where the angle is too small such that the frictional forces cannot be overcome with an acceptable amount of adjustment force, this can be described as self-locking. At the same time, it is desirable to use an angle that is close to the point of self-locking to achieve sufficient friction between interior surfaces (232, 234) and outer surface (220) when tightening wire (244) such that unintended slippage or movement between bushings (202, 204) and curved members (206, 208) is avoided and a secure tightening of flex arm (100) is achieved. Second bushings (204) have the same or similar features although second bushings (204) are larger than first bushings (202) as mentioned above. The description above regarding first bushings (202) applies to second bushings (204) as well.

First curved member (206) comprises bore (236) that extends through first curved member (206) and is defined by interior surface (238) of first curved member (206). As illustrated, bore (236) has a greater diameter at distal end (240) of first curved member (206), and the diameter then decreases to a minimum near the center of first curved member (206). When moving from the center further proximally through the bore (236) the diameter increases until reaching proximal end (242) of first curved member (206). Interior surface (238) is curved in a convex fashion giving bore (236) a concave/diverging shape and the appearance of an abstract hourglass turned on its side. In other words, the profile of interior surface (238) in section view resembles an hourglass on its side. Second curved members (208) have the same or similar features although second curved members (208) are larger than first curved members (206) as mentioned above. The description above regarding first curved members (206) applies to second curved members (208) as well.

With the shape and configuration of first and second curved members (206, 208) being somewhat elongated compared to a single sphere shape, there is more space or distance separation between one first bushing (202) and the following bushing (202). Similarly this is the case for the spacing or distance separation between second bushings (204) also. In some versions, the additional space or distance separation between consecutive bushings (202, 204) provides flex arm (100) with the ability to be flexed to tighter turns or turns having a smaller radius, without bushings (202, 204) becoming too close and binding against one another thereby restricting the range of adjustability.

Figure 5:
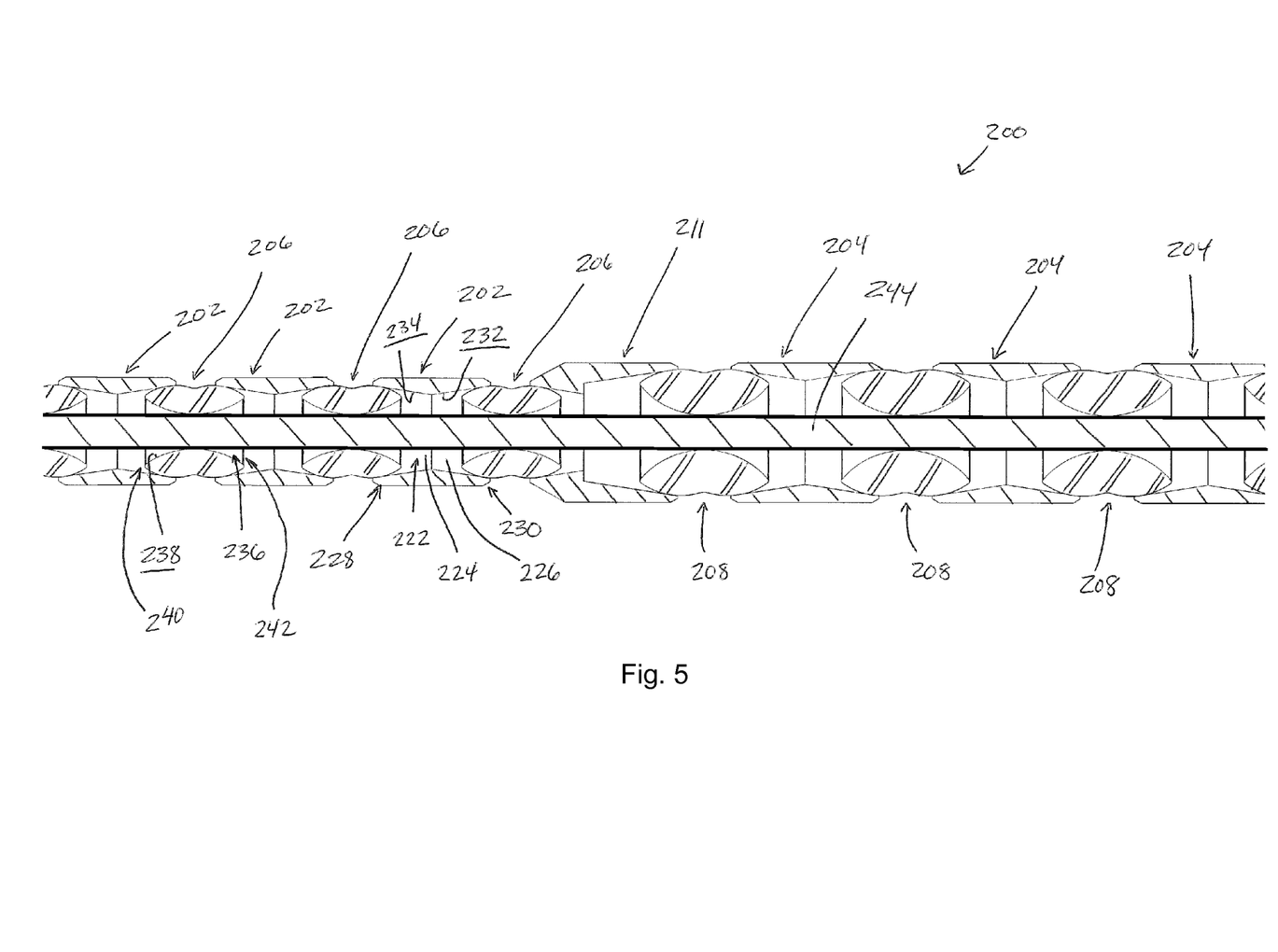
FIG. 5 depicts a side section view of a central portion of another example flexible arm similar to that shown in FIG. 1.

At the point of the smallest diameter of bore (236), or between opposing peaks of the convex surface of interior surface (238), the diameter of bore (236) is such that the diameter of wire or cable (244) matches (as shown in FIG. 5) or closely approximates (as shown in FIG. 3) the diameter of bore (236) at this point. As shown in the illustrated version, wire (244) extends through first and second curved members (206, 208) as well as through first and second bushings (202, 204) and reducer (211). Even though second curved members (208) are larger than first curved members (206), the diameter of the bores of second curved members (208) at the smallest point matches or closely approximates the diameter of wire (244). With this configuration, wire (244) is guided by first and second curved members (206, 208). In other words, there is no or very minimal space between the outer surface of wire (244) and interior surface (238) of bores (236) of first curved members (206) and also between outer surface of wire (244) and interior surface of bores of second curved members (208). This lack of space or very minimal space permits wire (244) to be guided by first and second curved members (206, 208) instead of wire (244) having the ability to shift position within excess space within first and second curved members of other versions. In view of the teachings herein, those of ordinary skill in the art will understand that wire (244) will seek to dissipate the tension or pressure it is under and one way of doing this is to shift position within any available excess space within first and second curved members. Thus by eliminating or reducing such excess space by having the diameter of bores (236) of first curved members (206) and the diameters of bores of second curved members (208) match or closely approximate the diameter of wire (244), wire (244) is prevented from shifting.

Because of the ability of first and second curved members (206, 208) to guide wire (244) as described above, flex arm (100) can be adjusted or flexed from one position to an alternate position without losing tension or pressure. Such adjustment can be done without loosening wire (244) using second adapter (408) as described below. Otherwise stated, the contact between wire (244) and bores (236) of first curved member (206) and bores of second curved member (208), along with the lack of space between these components as describe above, provides flex arm (100) with the ability to maintain tension or pressure even when being adjusted or flexed from one position to another position. As such, in some versions flex arm (100) is configured to be adjustable while maintaining constant or substantially constant tension within flex arm (100). However, flex arm (100) is also configured to be adjustable when changing tension within flex arm (100), or when not maintaining constant or substantially constant tension within flex arm (100).

When in use, flex arm (100) is generally adjustable using second actuator (408).

Second actuator (408) comprises knob (416) that can be rotated. Rotation of knob (416) causes wire (244) to translate along its longitudinal axis to either tighten or loosen flex arm (100). By way of example only, and not limitation, there may be a space within actuator (408) that provides room for wire (244) to translate. In some other versions actuator (408) can translate some amount when rotated and wire (244) can be connected, directly or indirectly, with actuator (408) such that it would undergo the same amount of translation. Still in some other versions, a lever and cam mechanism may be used to tighten and loosen wire (244) instead of actuator (408). In view of the teachings herein, various ways to tighten and loosen wire (244) using actuator (408) or another similar device will be apparent to those of ordinary skill in the art.

Also by way of example only, and not limitation, in some version a distal end of wire (244) connects within linking member (210) to fix wire (244) relative to linking member (210). In such versions, when wire (244) translates proximally based on rotation of knob (416), first and second curved members (206, 208) and first and second bushings (202, 204) are drawn closer together. This in turn causes contact between these components and the friction and pressure associated with the degree of contact causes flex arm (100) to be secured in position or locked in position. On the contrary, when wire (244) translates distally, for instance by rotating knob (416) in an opposite direction, first and second curved members (206, 208) and first and second bushings (202, 204) are moved further apart, or at least the degree of contact between these components is lessened. This in turn causes a decrease in friction and pressure associated with the degree of contact between these components and as such flex arm (100) is in a readily adjustable state or unlocked position or state where flex arm (100) can be positioned as desired before tightening wire (244) to secure the position of flex arm (100). In view of the teachings herein, it will be apparent to those of ordinary skill in the art that the tension in flex arm (100) is directly related to the degree of friction and contact between curved members (206, 208) and bushings (202, 204).

As mentioned above, in some versions flex arm (100) need not be loosened via actuator (408) to make an adjustment or flex or position change in flex arm (100). Again, because of the ability of first and second curved members (206, 208) to guide wire (244), along with the lack of space for wire to shift around, the tension or pressure of flex arm (100) in the secured state can be maintained such that flex arm (100) can be adjusted or flexed to an alternate position or shape even without using second actuator (408) to relieve the tension or pressure of the system. Again, second actuator (408) is configured to relive the tension or pressure of the system by translating wire (244) to thereby alter the spacing of curved members (206, 208) and bushings (202, 204), which alters the frictional forces within the system.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

I claim:

1. A flexible arm for use in a medical procedure, wherein the flexible arm comprises:
   (a) a plurality of first members, wherein each of the first members comprise a first bore extending through the respective first member, wherein the first bore defines an interior region having a first end, a second end opposite the first end, and a middle, wherein the first bore includes a varying diameter along the interior region from the first and second ends to the middle; and
   (b) a plurality of second members, wherein each of the second members comprise:
      (i) a first curved portion, (ii) a second curved portion, wherein each of the first curved portion and the second curved portion comprise a first end and a second end, wherein each of the first curved portion and the second curved portion comprise a varying outer diameter that increases then decreases from the first end to the second end, (iii) a center portion where the first curved portion and the second curved portion meet, wherein the varying outer diameter of both the first curved portion and the second curved portion decreases when approaching the center portion, and (iv) a second bore that extends through the first curved portion and the second curved portion, wherein the second bore comprises a longitudinal axis, a first diameter and a second diameter, wherein the second diameter is larger than the first diameter; and wherein at least a portion of the first curved portion and at least a portion of the second curved portion are configured to fit within the interior region of a respective one of the first members.

2. The flexible arm of claim 1, wherein each of the first members engage a first exterior surface of the first curved portion of a respective one of the second members, and wherein each of the first members further engage a second exterior surface of the second curved portion of a respective one of the second members.

3. The flexible arm of claim 1, further comprising a wire extending through each of the first members and each of the second members, wherein the wire is adjustable to selectively increase contact between the first curved portion and the second curved portion of the second members with the interior region of a respective one of the first members.

4. The flexible arm of claim 1, wherein the interior region of each of the first members comprises a first angled portion and a second angled portion.

5. The flexible arm of claim 4, wherein the first curved portion and the second curved portion of the second members engage the first angled portion and the second angled portion of a respective one of the first members.

6. The flexible arm of claim 1, wherein the plurality of first members comprises a first set of first members and a second set of first members that are larger than the first set of first members, wherein the plurality of second members comprises a first set of second members and a second set of second members that are larger than the first set of second members, wherein the flexible arm further comprises a reducer positioned on the flexible arm to transition from the second set of first members and the second set of second members to the first set of first members and the first set of second members.

7. The flexible arm of claim 1, wherein the interior region of each of the first members is defined by interior conical surfaces.

8. The flexible arm of claim 1, wherein the first diameter of the second bore is located near a midpoint along the longitudinal axis of the second bore.

9. A flexible arm for use in a medical procedure, wherein the flexible arm comprises:

(a) a plurality of bushings, wherein the bushings each comprise a bore extending through each of the bushings, wherein a longitudinal cross-sectional profile of each of the plurality of bushings defines a continuous planar interior sidewall that extends from a central portion to an outermost end of the interior sidewall defined by an exterior surface of the respective bushing, wherein the bore of each of the plurality of bushings comprises opposing and directly connected conical surfaces that extend to the outermost end;

(b) a plurality of curved members, wherein the curved members are positioned between the bushings, wherein the curved members each comprise a curvilinear bore extending through each of the curved members; and (c) a wire, wherein the wire extends through each of the bushings and each of the curved members, wherein the wire is adjustable between a first position and a second position, wherein a diameter of the wire matches the diameter of the curvilinear bore of the curved members at its smallest point such that contact is continuously maintained between an outer surface of the wire and an interior surface of the curvilinear bore.

10. The flexible arm of claim 9, wherein a diameter of the curvilinear bore of each of the curved members varies.

11. The flexible arm of claim 9, wherein each of the curved members at least partially fit within the curvilinear bore of a respective one of the bushings.

12. The flexible arm of claim 9, wherein the wire imparts a first amount of force upon each of the bushings and the curved members when the wire is in the first position, and wherein the wire imparts a second amount of force upon each of the bushings and the curved members when the wire is in the second position.

13. The flexible arm of claim 9, wherein the flexible arm further comprises an actuator operable to adjust the wire.

14. The flexible arm of claim 9, wherein the curved members each comprise a first curved portion, a second curved portion, and a center portion positioned between the first and second curved portions, wherein the center portion has a smaller outer diameter than at least a portion of the first and second curved portions.

15. The flexible arm of claim 9, wherein the contact between the outer surface of the wire and the interior surface of each curvilinear bore guides the wire whether the wire is in the first or second position such that the flexible arm is adjustable without loss of tension in the wire.

16. A flexible arm for use in a medical procedure, wherein the flexible arm comprises:

(a) a plurality of first members, wherein each of the first members comprise an interior region, an interior surface, and a longitudinal axis, wherein a longitudinal cross-sectional profile of the interior surface defines a continuous planar interior sidewall that extends from a central portion to an outermost end of the interior sidewall defined by an exterior surface of the first member, wherein the interior region of the plurality of first members comprises opposing and directly connected conical surfaces that extend to the outermost end; and (b) a plurality of second members, wherein each of the second members is configured to fit within the interior region of at least one of the plurality of first members.

17. The flexible arm of claim 16, wherein each of the second members are configured to tangentially contact the interior surface of at least one of the first members.

18. The flexible arm of claim 16, wherein one of the second members is configured to fit within the interior region of two sequentially positioned first members.

19. The flexible arm of claim 16, wherein the continuous planar interior sidewall defines an angle with respect to the longitudinal axis, wherein the angle is less than 20 degrees.

20. The flexible arm of claim 16, wherein the interior region of each of the first members comprises a first region and a second region, wherein the first and second regions each have a conical shape.

* * * * *